(12) United States Patent
Hatsuda

(10) Patent No.: US 11,980,378 B2
(45) Date of Patent: May 14, 2024

(54) CALCULUS CRUSHING DEVICE

(71) Applicant: OLYMPUS CORPORATION, Tokyo (JP)

(72) Inventor: Tomoki Hatsuda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 750 days.

(21) Appl. No.: 17/117,382

(22) Filed: Dec. 10, 2020

(65) Prior Publication Data

US 2021/0093343 A1  Apr. 1, 2021

Related U.S. Application Data

(63) Continuation of application No. PCT/JP2018/024182, filed on Jun. 26, 2018.

(51) Int. Cl.
*A61B 17/22* (2006.01)
*A61B 17/221* (2006.01)

(52) U.S. Cl.
CPC ...... *A61B 17/22022* (2013.01); *A61B 17/221* (2013.01); *A61B 2017/22025* (2013.01); *A61B 2017/2215* (2013.01)

(58) Field of Classification Search
CPC ............ A61B 17/221; A61B 17/22022; A61B 2017/2212; A61B 2017/2215; A61B 2017/22025; A61B 2017/00477; A61B 17/320758; A61B 17/320725; A61B 2017/320766; A61B 2017/320733
See application file for complete search history.

(56) References Cited

U.S. PATENT DOCUMENTS

2008/0009884 A1   1/2008   Kennedy, II
2008/0033467 A1   2/2008   Miyamoto et al.
(Continued)

FOREIGN PATENT DOCUMENTS

CN    106999193 A    8/2017
EP    1864618 A1    12/2007
(Continued)

OTHER PUBLICATIONS

International Search Report dated Sep. 18, 2018 issued in PCT/JP2018/024182.

*Primary Examiner* — Majid Jamialahmadi
(74) *Attorney, Agent, or Firm* — Scully, Scott, Murphy & Presser, P.C.

(57) ABSTRACT

A device includes: a sheath; an operating wire disposed inside the sheath; a grasping part that is provided at a distal end of the operating wire and that has one or more wires; and a bipolar electrode disposed at a distal end of the sheath. The sheath has, at intervals in the circumferential direction, escape grooves that extend from the distal end toward a proximal end of the sheath, that penetrate from an inner circumferential surface to an outer circumferential surface thereof, and that have such dimensions as to allow the wires to pass therethrough. The bipolar electrode is disposed at a position shifted radially outward from the central axis and at a position between two of the escape grooves in the circumferential direction. The distal end of the bipolar electrode is positioned closer to distal ends of the escape grooves than to proximal ends of the escape grooves.

20 Claims, 15 Drawing Sheets

(56) References Cited

U.S. PATENT DOCUMENTS

| | | | |
|---|---|---|---|
| 2010/0286709 A1* | 11/2010 | Diamant | A61B 17/22012 606/128 |
| 2013/0060169 A1 | 3/2013 | Yamada et al. | |
| 2013/0079797 A1 | 3/2013 | Diamant, I et al. | |
| 2014/0257144 A1 | 9/2014 | Capelli et al. | |
| 2014/0257323 A1 | 9/2014 | Mantell | |
| 2016/0016013 A1 | 1/2016 | Capelli et al. | |
| 2017/0252052 A1 | 9/2017 | Okada | |
| 2020/0316409 A1 | 10/2020 | Capelli et al. | |

FOREIGN PATENT DOCUMENTS

| | | |
|---|---|---|
| EP | 3 275 380 A1 | 1/2018 |
| EP | 3626307 A1 | 3/2020 |
| JP | S58-032756 A | 2/1983 |
| JP | S62-041724 B2 | 9/1987 |
| JP | 2000-333967 A | 12/2000 |
| JP | 2006-314715 A | 11/2006 |
| JP | 2007-325925 A | 12/2007 |
| JP | 2009-541006 A | 11/2009 |
| JP | 2016-508851 A | 3/2016 |
| WO | WO 2008/002417 A2 | 1/2008 |
| WO | WO 2009/074981 A1 | 6/2009 |
| WO | WO 2012/063825 A1 | 5/2012 |
| WO | WO 2014/138582 A2 | 9/2014 |
| WO | WO 2014/140715 A2 | 9/2014 |

\* cited by examiner

CALCULUS CRUSHING DEVICE

CROSS-REFERENCE TO RELATED APPLICATIONS

This is a continuation of International Application PCT/JP2018/024182, with an international filing date of Jun. 26, 2018, which is hereby incorporated by reference herein in its entirety.

TECHNICAL FIELD

The present invention relates to a calculus crushing device.

BACKGROUND ART

There is a known calculus crushing device that is inserted through a channel of an endoscope to endoscopically perform treatment when a calculus formed in an organ, such as the bile duct and the urinary bladder, is crushed (for example, see PTL 1).

Furthermore, a calculus crushing device, in which a basket wire is made to protrude from an inner hole of a short-tubular rigid distal-end tip fixed to a distal end of a flexible tube, has a disadvantage in that, when a calculus accommodated inside the basket wire is crushed, the basket wire is caught between the distal-end tip and the calculus, and a force is not transmitted to the basket wire; thus, in order to solve this disadvantage, there is a known calculus crushing device that has, at a distal-end tip, an escape groove into which a basket wire is inserted (for example, see PTL 2).

CITATION LIST

Patent Literature

{PTL 1} Japanese Unexamined Patent Application, Publication No. 2006-314715
{PTL 2} Japanese Examined Utility Model Application, Publication No. Sho 62-41724

SUMMARY OF INVENTION

One aspect of the present invention is directed to a calculus crushing device including: a tubular sheath that has a central axis; an operating wire that is disposed inside the sheath so as to be movable along the central axis; a grasping part that is provided at a distal end of the operating wire and that has one or more wires; and at least one bipolar electrode that is disposed at a distal end of the sheath and that applies a shock to a processing target grasped by the grasping part, wherein the sheath has, at intervals in a circumferential direction, a plurality of escape grooves that extend from the distal end of the sheath toward a proximal end of the sheath, that penetrate from an inner circumferential surface of the sheath to an outer circumferential surface thereof, and that have such dimensions as to allow the wires of the grasping part to pass therethrough; the at least one bipolar electrode is disposed at a position shifted radially outward from the central axis and at a position between two of the escape grooves in the circumferential direction; a distal end of the at least one bipolar electrode is positioned closer to distal ends of the escape grooves than to proximal ends of the escape grooves; and the distal end of the at least one bipolar electrode is disposed at a position close to a surface of the processing target in a state in which the processing target abuts against the distal end of the sheath.

Another aspect of the present invention is directed to a calculus crushing device including: a tubular sheath that has a central axis; an operating wire that is disposed inside the sheath so as to be movable along the central axis; a grasping part that is provided at a distal end of the operating wire and that has one or more wires; and a plurality of bipolar electrodes that are disposed at a distal end of the sheath and that apply shocks to a calculus grasped by the grasping part, wherein the sheath has, at intervals in a circumferential direction, a plurality of escape grooves that extend from the distal end of the sheath toward a proximal end of the sheath, that penetrate from an inner circumferential surface of the sheath to an outer circumferential surface thereof, and that have such dimensions as to allow the wires of the grasping part to pass therethrough; the bipolar electrodes are each disposed at a position shifted radially outward from the central axis and at a position between two of the escape grooves in the circumferential direction and are disposed at positions so as to sandwich at least one of the escape grooves in the circumferential direction; and distal ends of the bipolar electrodes are positioned closer to distal ends of the escape grooves than to proximal ends of the escape grooves.

DESCRIPTION OF EMBODIMENT

A calculus crushing device 1 according to a first embodiment of the present invention will be described below with reference to the drawings.

Figure 1:
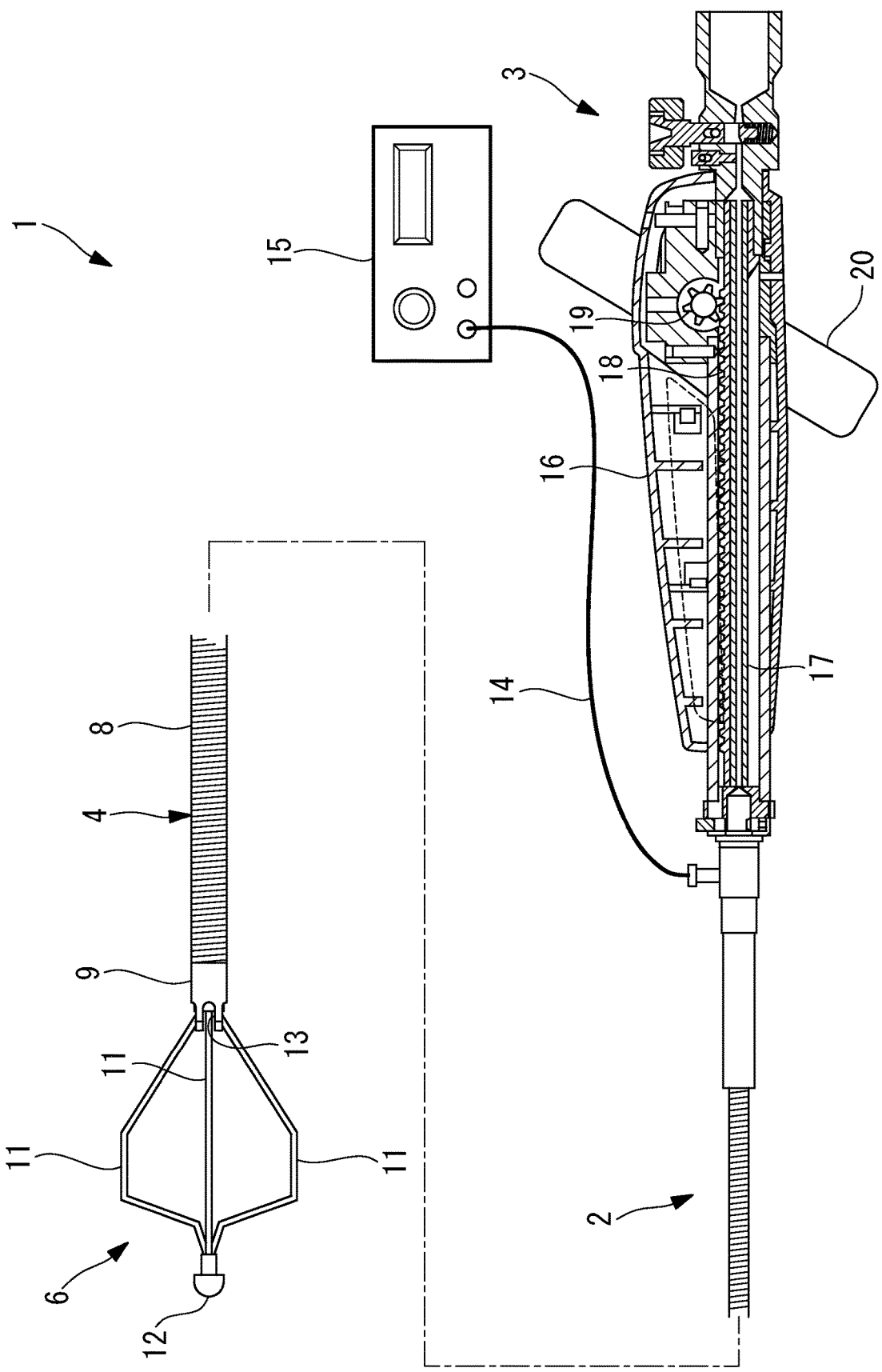
FIG. 1 is a view showing the overall configuration of a calculus crushing device according to one embodiment of the present invention.

As shown in FIG. 1, the calculus crushing device 1 of this embodiment includes a long insertion portion 2 and an operating portion 3 that is fixed to a proximal end of the insertion portion 2. In the figure, reference sign 15 denotes a power source that supplies electric power to bipolar electrodes 7 to be described later.

The insertion portion 2 includes: a tubular sheath 4; an operating wire 5 that is disposed inside the sheath 4 so as to be movable along a central-axis direction of the sheath 4; a basket wire (grasping part) 6 that is provided at a distal end of the operating wire 5; and the bipolar electrodes 7, which are disposed at a distal end of the sheath 4.

The sheath 4 includes: a coil sheath 8 that has such flexibility as to be able to be bent along an insertion path, for example, and that has a high compressive strength; and a distal-end tip 9 that is fixed to a distal end of the coil sheath 8. The distal-end tip 9 is a cylindrical member formed of metal and is coaxially fixed to the distal end of the sheath by a cylindrical connection member.

The operating wire 5 is disposed over the entire length of the sheath 4 and is pulled toward the proximal end by the operating portion 3, which is attached to the proximal end of the sheath 4.

Figure 2:
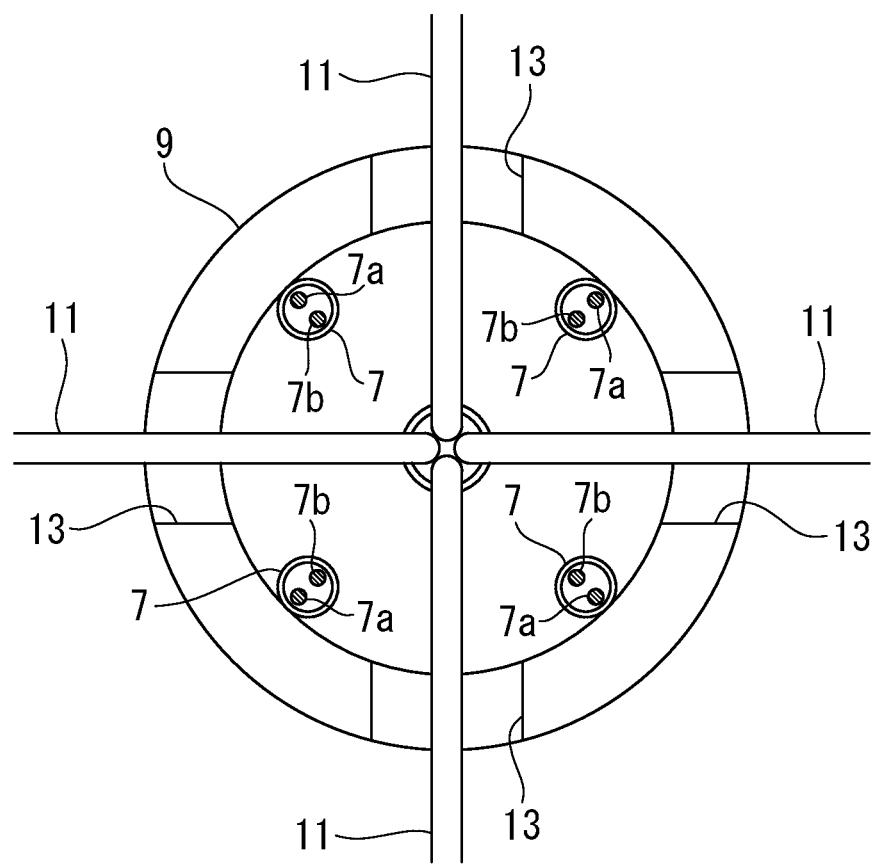
FIG. 2 is a view of a distal-end tip of the calculus crushing device shown in FIG. 1, viewed from the distal end.

As shown in FIGS. 1 and 2, for example, the basket wire 6 includes: four wires 11, proximal end sections of which are bundled at the distal end of the operating wire 5; and a distal-end member 12 that bundles distal-end sections of the wires 11. The wires 11 are folded, thereby being allowed to be accommodated inside the sheath 4, and are pushed forward from the inside of the sheath 4, thereby expanding, as shown in FIG. 1, and forming a basket so as to surround a predetermined space.

Figure 3:
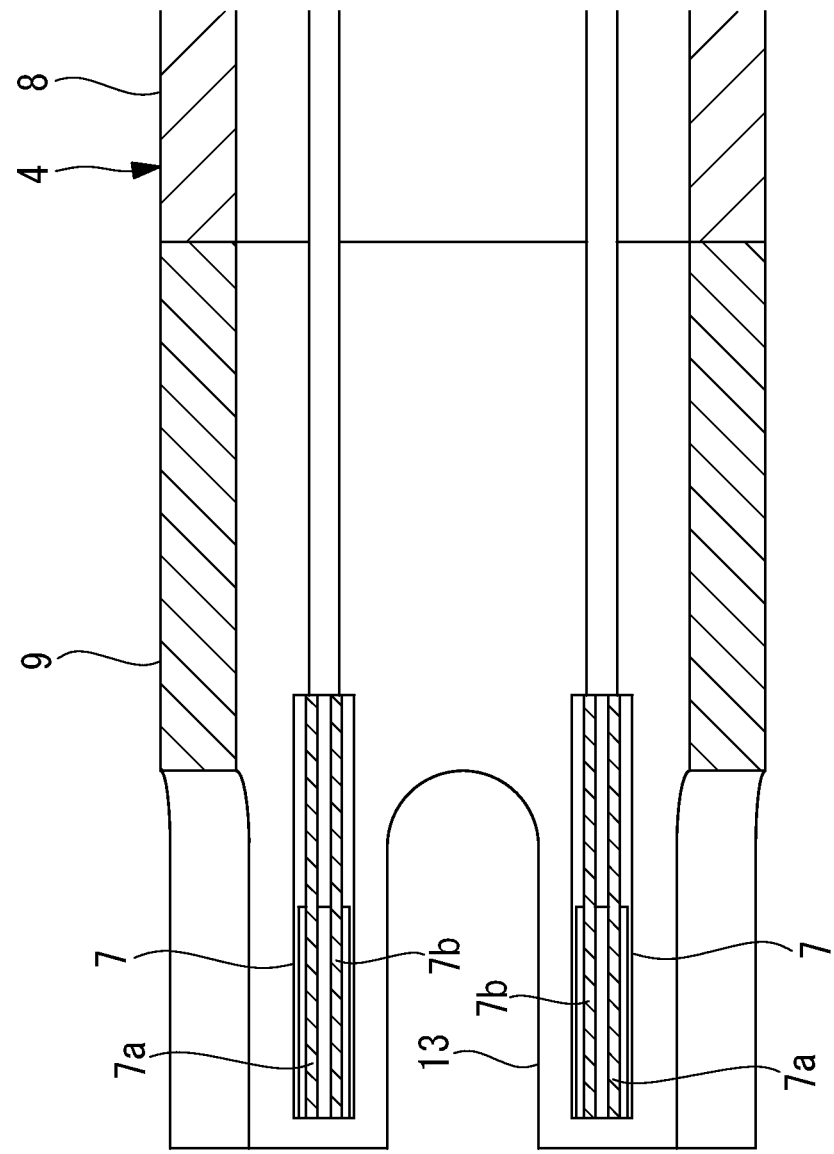
FIG. 3 is a partial longitudinal sectional view showing the relationship between the distal-end tip of the calculus crushing device shown in FIG. 2 and bipolar electrodes.
Figure 4:
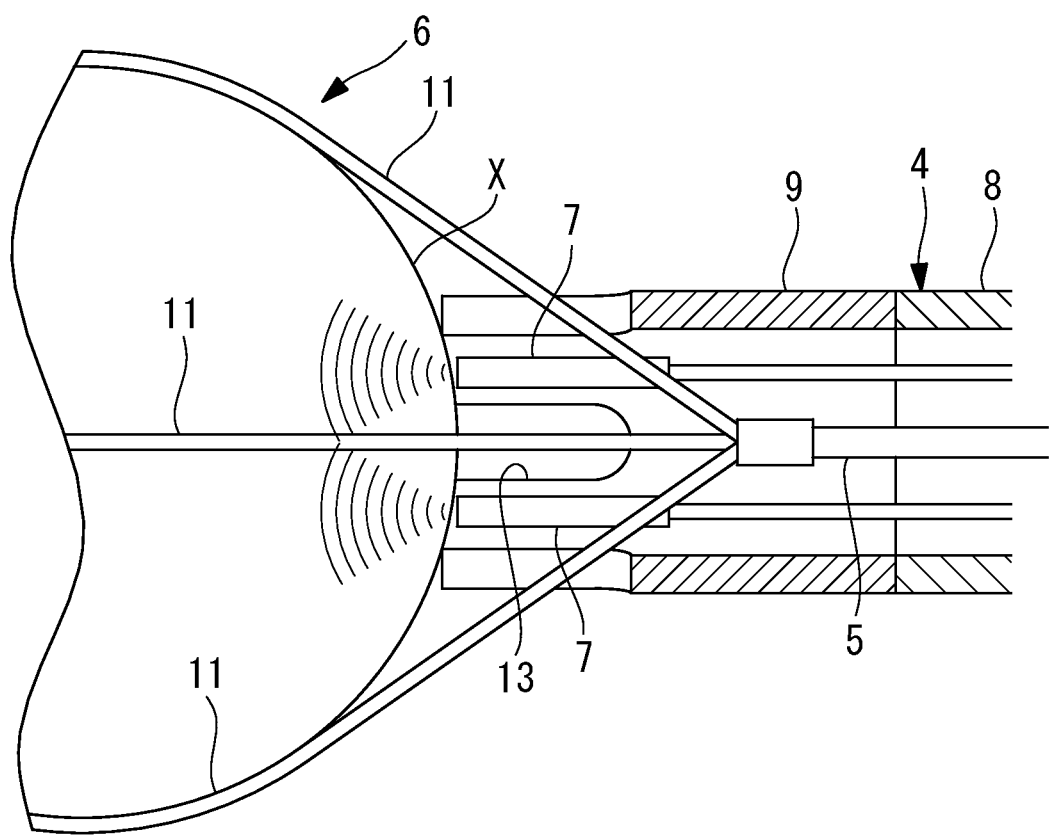
FIG. 4 is a partial longitudinal sectional view of a distal-end section of the calculus crushing device shown in FIG. 1.

As shown in FIGS. 2 to 4, the distal-end tip 9 includes: four escape grooves 13 that extend from the distal end toward the proximal end; and protruding sections (electrode placement sections) that extend, between the escape grooves 13, from the proximal ends of the escape grooves 13 toward distal ends thereof. The respective escape grooves 13 penetrate the distal-end tip 9 from an inner circumferential surface to an outer circumferential surface and extend parallel to the central axis up to a predetermined position in the central-axis direction. In the example shown in FIGS. 2 and 3, the escape grooves 13 are provided at four places at intervals in the circumferential direction in order to accommodate the four wires 11, which constitute the basket wire 6.

The escape grooves 13 each have a groove width dimension greater than the diameter of each of the wires 11 that constitute the basket wire 6.

The bipolar electrodes 7 each include a positive electrode (electrode) 7a and a negative electrode (electrode) 7b. In the bipolar electrode 7, it is preferred that the number of positive electrodes (electrodes) 7a and the number of negative electrodes (electrodes) 7b be the same. In this embodiment, as shown in FIG. 2, a description will be given of an example case in which the positive electrode 7a and the negative electrode 7b form a pair. When electric power is supplied, the bipolar electrodes 7 are used to generate a spark in a liquid, such as bile or a contrast agent, that includes a calculus X, to apply a shock to the calculus X with shock waves propagating in the liquid.

As shown in FIG. 2, the bipolar electrodes 7 are each provided on a distal-end inner surface of the distal-end tip 9, at four positions that are shifted radially outward from the central axis and that are on the protruding sections, which are provided between the escape grooves 13 in the circumferential direction. As shown in FIG. 4, the distal ends of the bipolar electrodes 7 are located closer to the distal ends of the escape grooves 13 than to the proximal ends of the escape grooves 13, and, in a state in which the calculus X is made to abut against a distal-end face of the distal-end tip 9, the distal ends of the bipolar electrodes 7 are disposed close to the surface of the calculus X, at four positions at intervals in the circumferential direction. The individual bipolar electrodes 7 are connected to the power source 15, which is located at a position close to the proximal end, by a cable 14 that penetrates through the sheath 4.

As shown in FIG. 1, for example, the operating portion 3 includes: a main body 16 that is connected to the proximal end of the sheath 4; a combining member 17 that is provided so as to be movable in the front-back direction with respect to the main body 16 and that is connected to the operating wire 5; and a handle 20 that includes a pinion gear 19 that is engaged with a rack gear 18 provided on the combining member 17. Furthermore, a switch (not shown) is disposed on the operating portion 3, and electric current can be carried from the power source 15 to the bipolar electrodes 7 by operating the switch.

To operate the operating portion 3, for example, the main body 16 is grasped with the left hand, and the handle 20 is rotated with the right hand, thereby rotating the pinion gear 19, which is fixed to the handle 20, and moving the rack gear 18, with which the pinion gear 19 is engaged, toward the proximal end of the main body 16. Accordingly, the combining member 17, to which the rack gear 18 is fixed, is moved toward the proximal end of the main body 16, and the operating wire 5, which is fixed to the combining member 17, is pulled toward the proximal end.

The operation of the thus-configured calculus crushing device 1 of this embodiment will be described below.

In order to crush the calculus X in the body of a patient by using the calculus crushing device 1 of this embodiment, the operating portion 3, which is disposed at the proximal end of the sheath 4, is operated to pull the basket wire 6 into the sheath 4, thus putting the basket wire 6 in a contracted state, the insertion portion is inserted through a channel of an endoscope (not shown) inserted into a body cavity, and the distal end of the distal-end tip 9 of the calculus crushing device 1 is disposed close to the calculus X in the body.

In this state, the operator operates the operating portion 3, which is disposed outside the body of the patient, to push the operating wire 5 toward the distal end, thus making the basket wire 6 protrude from the distal end of the distal-end tip 9. The basket wire 6 is pushed frontward from the distal-end tip 9, thereby being released from the contracted state and being expanded. In this state, the calculus X is accommodated inside the basket wire 6, and the operating portion 3 is operated to pull the operating wire 5 toward the proximal end.

When the operating wire 5 is pulled toward the proximal end, the respective wires 11, which constitute the basket wire 6, are drawn into the distal-end tip 9. Then, after the calculus X grasped by the basket wire 6 is pulled up to a position at which the calculus X abuts against the distal-end tip 9, the switch is operated to supply electric power to the bipolar electrodes 7 from the power source 15.

Accordingly, a spark is generated at the bipolar electrodes 7 close to the surface of the calculus X that has abutted against the distal-end tip 9, thus applying a shock to the calculus X with shock waves, which propagate inside the liquid. Then, because cracks occur in the calculus X to which a shock has been applied, thereafter, the handle 20 is further rotated with respect to the main body 16 to further apply a pulling force to the operating wire 5, thereby crushing the calculus X bound between the basket wire 6 and the distal end of the distal-end tip 9. Furthermore, when a shock is applied to the calculus X, the calculus X may also be held in a tightened state by the basket wire 6.

In this state, because the escape grooves 13 are provided in the distal-end tip 9, and the respective wires 11 are accommodated inside the escape grooves 13, even when the operating wire 5 is pulled until the calculus X abuts against the distal end of the distal-end tip 9, the respective wires 11, which constitute the basket wire 6, are prevented from being caught between the calculus X and the distal-end tip 9.

Then, because the calculus X is put in such a state as to be easily crushed by a shock, without a large tensile force being applied to the respective wires 11, which constitute the basket wire 6, there is an advantage in that the tensile force to be applied to the wires 11 when the calculus X is crushed can be small, and the wires 11 are prevented from being plastically deformed even when the wires 11 are subjected to friction with inner walls of the proximal ends of the escape grooves 13.

In particular, according to the calculus crushing device 1 of this embodiment, because the bipolar electrodes 7 are disposed on the inner surface of the distal-end tip 9, it is possible to apply shocks at the positions radially away from the central axis of the distal-end tip 9. Accordingly, because shocks are applied at the vicinities of the positions at which the calculus X is bound by the wires 11, there is an advantage in that the calculus X can be easily crushed through being bound.

Figure 5:
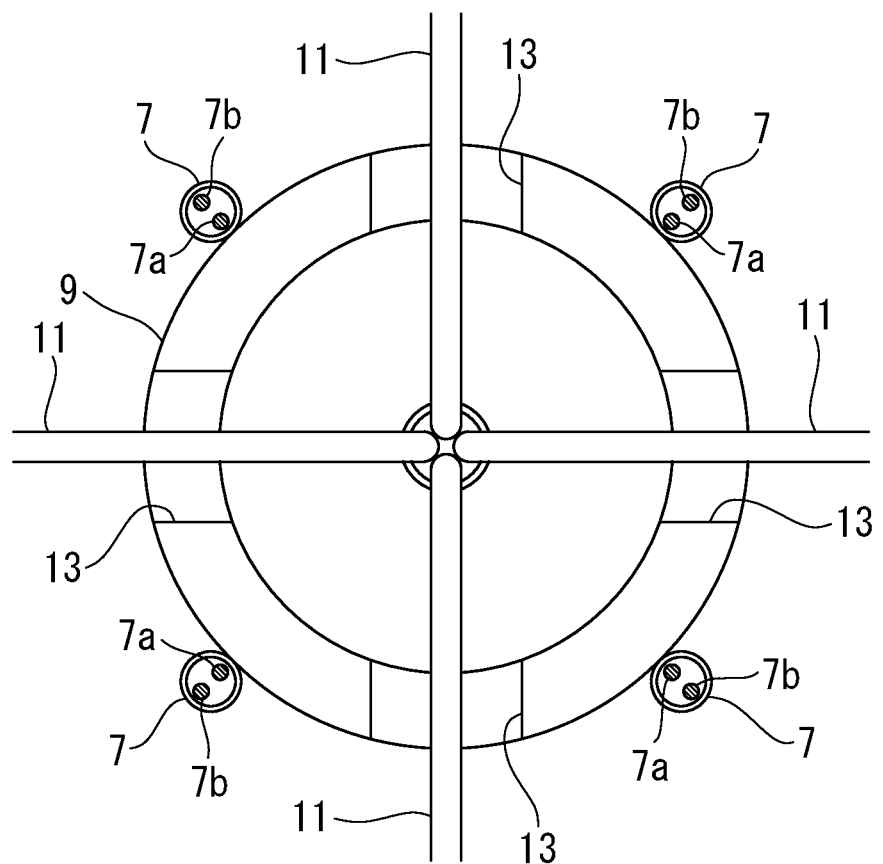
FIG. 5 is a view of a distal-end tip viewed from the distal end, showing a first modification of the calculus crushing device shown in FIG. 1.
Figure 6:
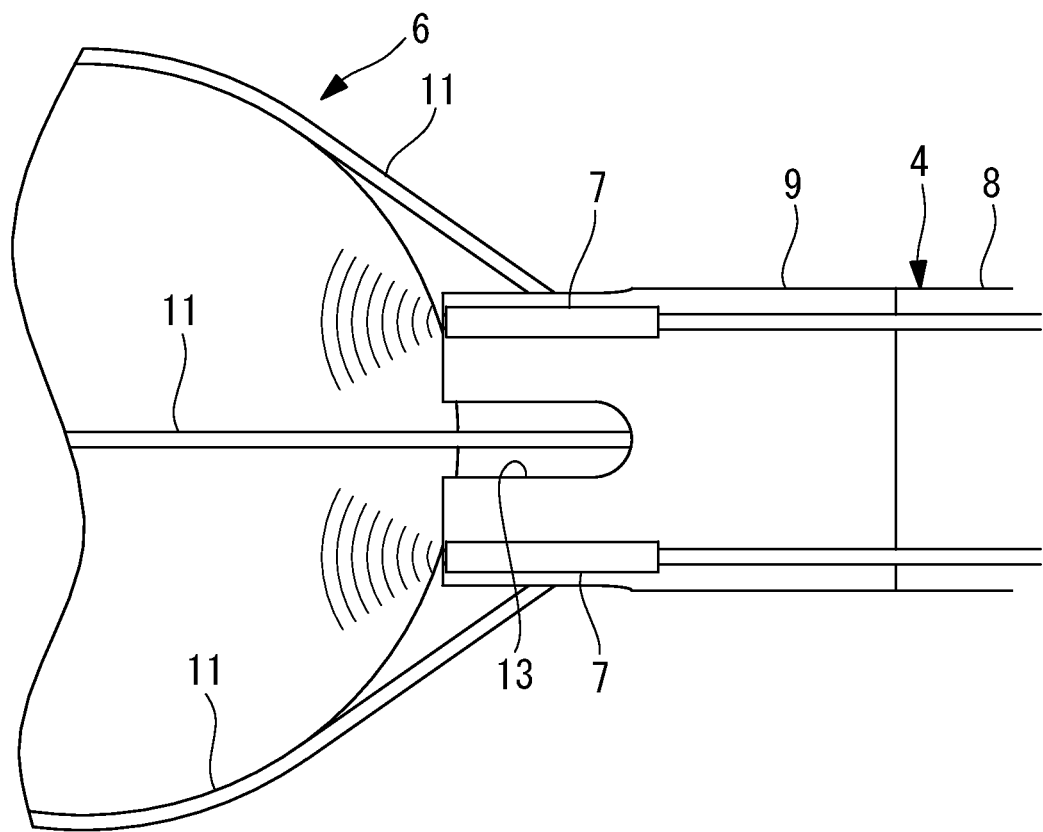
FIG. 6 is a partial side view of a distal-end section, showing a calculus crushing device shown in FIG. 5.

Note that, in this embodiment, the bipolar electrodes 7 are disposed on the inner surface of the distal-end tip 9. Accordingly, the cable 14, which connects the bipolar electrodes 7 and the power source 15, can be routed through the inside of the sheath 4. Instead of this, as shown in FIGS. 5 and 6, the bipolar electrodes 7 may be disposed on an outer surface of the distal-end tip 9. Accordingly, there is an advantage in that the bipolar electrodes 7 can be disposed at positions further away from the central axis of the distal-end tip 9 in radial directions, and regions where shocks are applied to the calculus X can be made closer to the positions at which the calculus X is bound by the wires 11.

Figure 7:
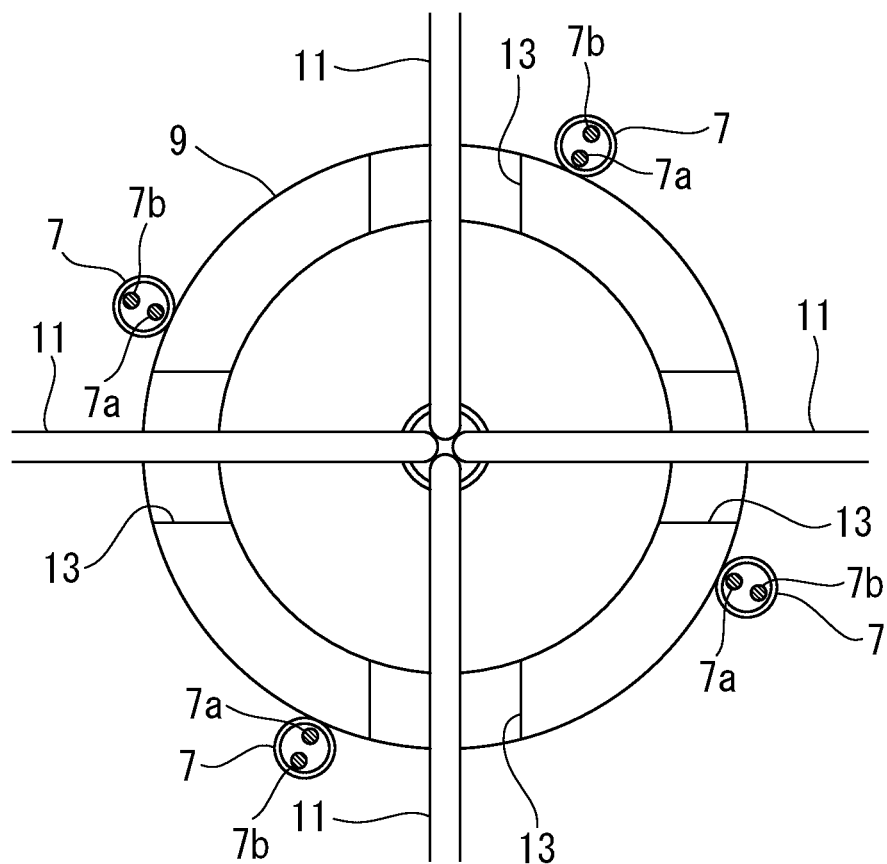
FIG. 7 is a view of a distal-end tip viewed from the distal end, showing a second modification of the calculus crushing device shown in FIG. 1.

Furthermore, in the examples shown in FIGS. 2 and 5, although the bipolar electrodes 7 are each disposed at the center position between the adjacent wires 11, instead of this, as shown in FIG. 7, it is also possible to dispose each of the bipolar electrodes 7 at a position close to one of the adjacent wires 11 in the circumferential direction, i.e., at a position closer to one of the two adjacent escape grooves 13 than to the center position between the two adjacent escape grooves 13, in the circumferential direction. Accordingly, there is an advantage in that the regions where shocks are applied to the calculus X can be made closer to the positions at which the calculus X is bound by the wires 11, thus making it possible to easily crush the calculus X through being bound.

Figure 8:
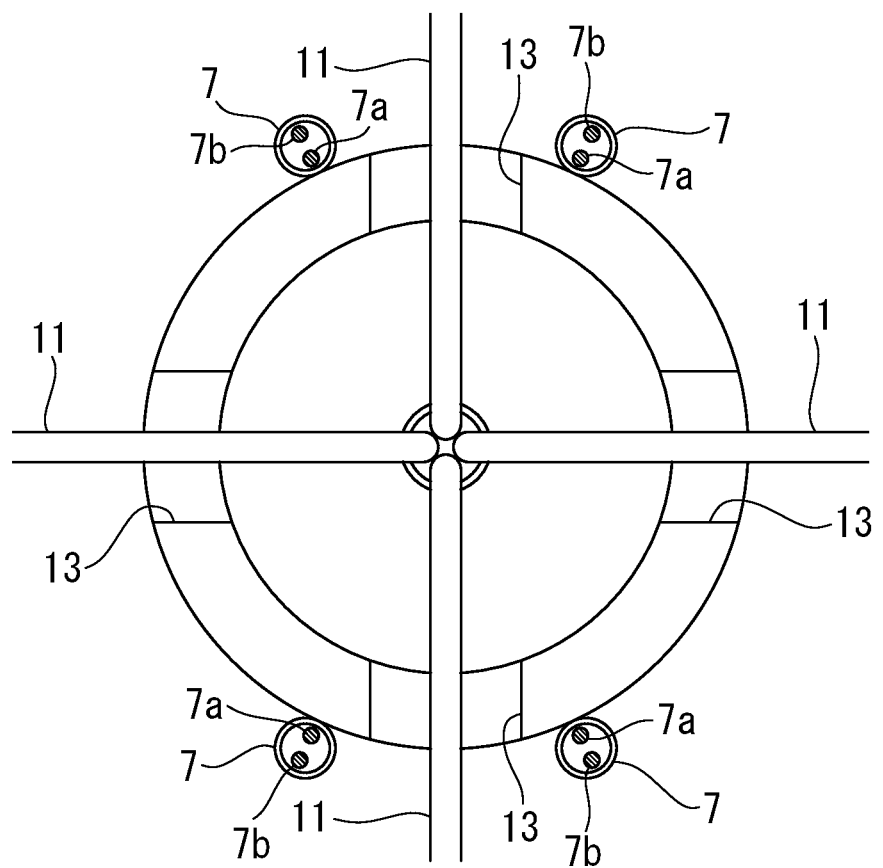
FIG. 8 is a view of a distal-end tip viewed from the distal end, showing a third modification of the calculus crushing device shown in FIG. 1.
Figure 9:
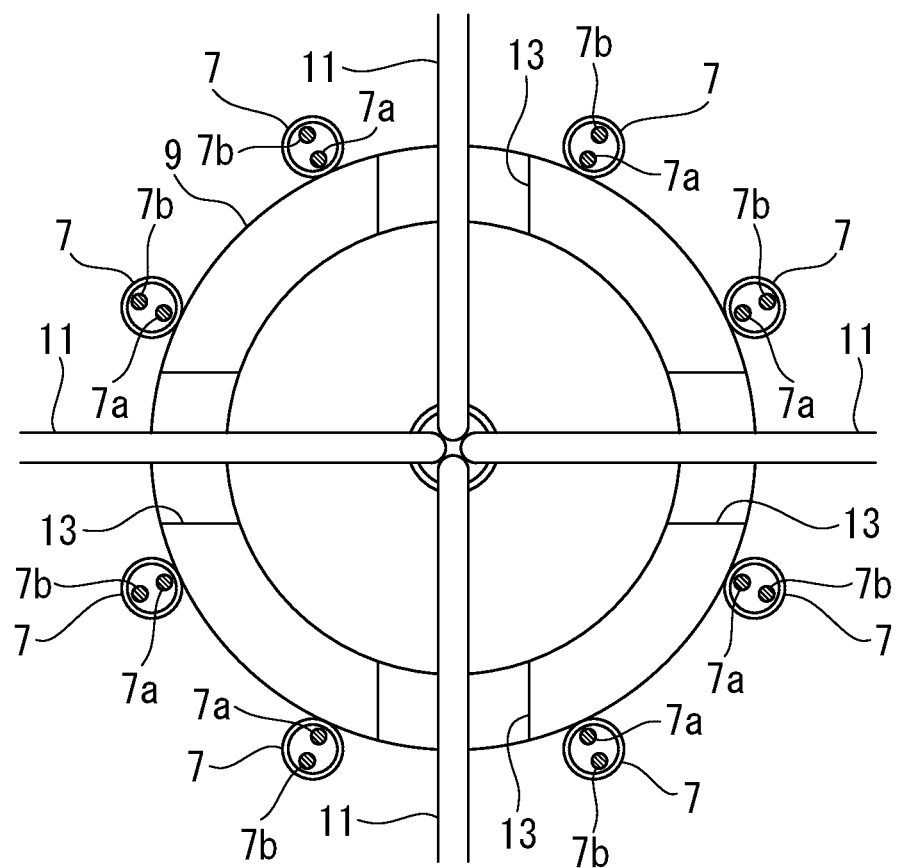
FIG. 9 is a view of a distal-end tip viewed from the distal end, showing a fourth modification of the calculus crushing device shown in FIG. 1.

Furthermore, as shown in FIG. 8, the bipolar electrodes 7 may be disposed at positions close to both sides of any of the wires 11 in the circumferential direction. Furthermore, as shown in FIG. 9, the bipolar electrodes 7 may be disposed at positions close to both sides of each of the wires 11 so as to sandwich the wire 11 in the circumferential direction.

Figure 10:
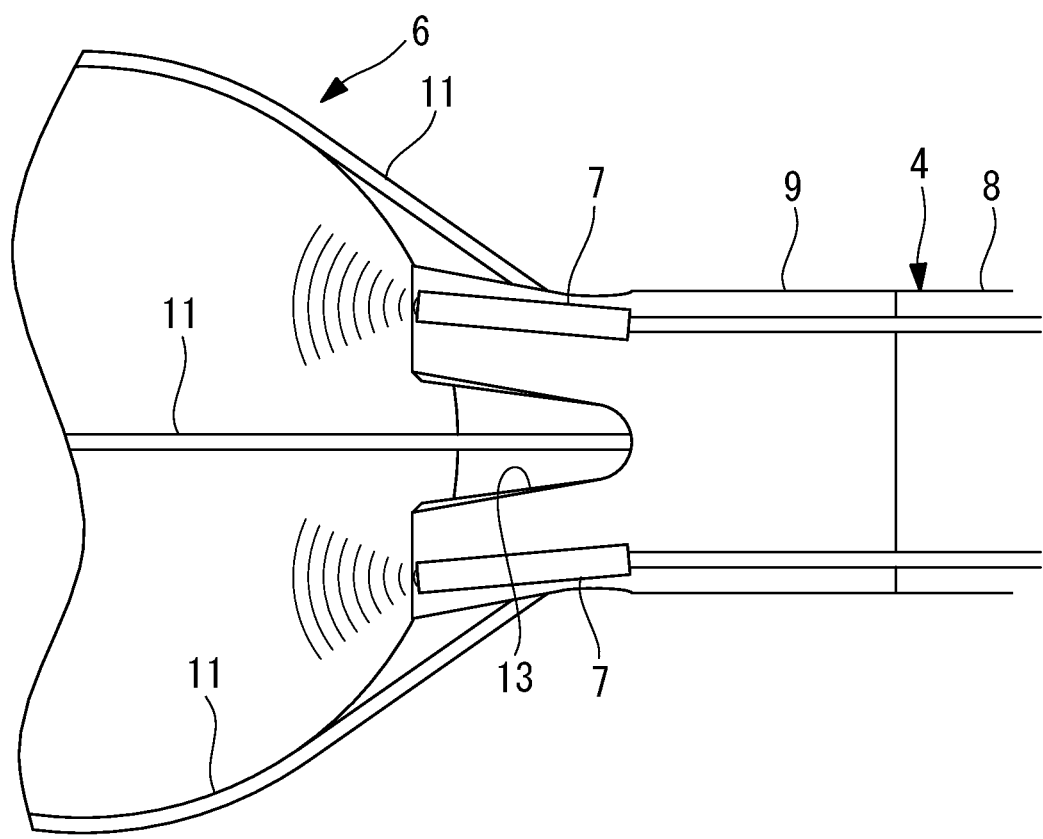
FIG. 10 is a partial side view of a distal-end section, showing a fifth modification of the calculus crushing device shown in FIG. 1.

Furthermore, as shown in FIG. 10, the distal end of the distal-end tip 9 may be inclined in such directions as to expand toward the distal end. Accordingly, the distal ends of the bipolar electrodes 7 that are disposed on the outer circumferential surface of the distal-end tip 9 can be disposed in such orientations as to face obliquely outward, thus making it possible to shift the regions where shocks are applied to the calculus X further outward.

Figure 11:
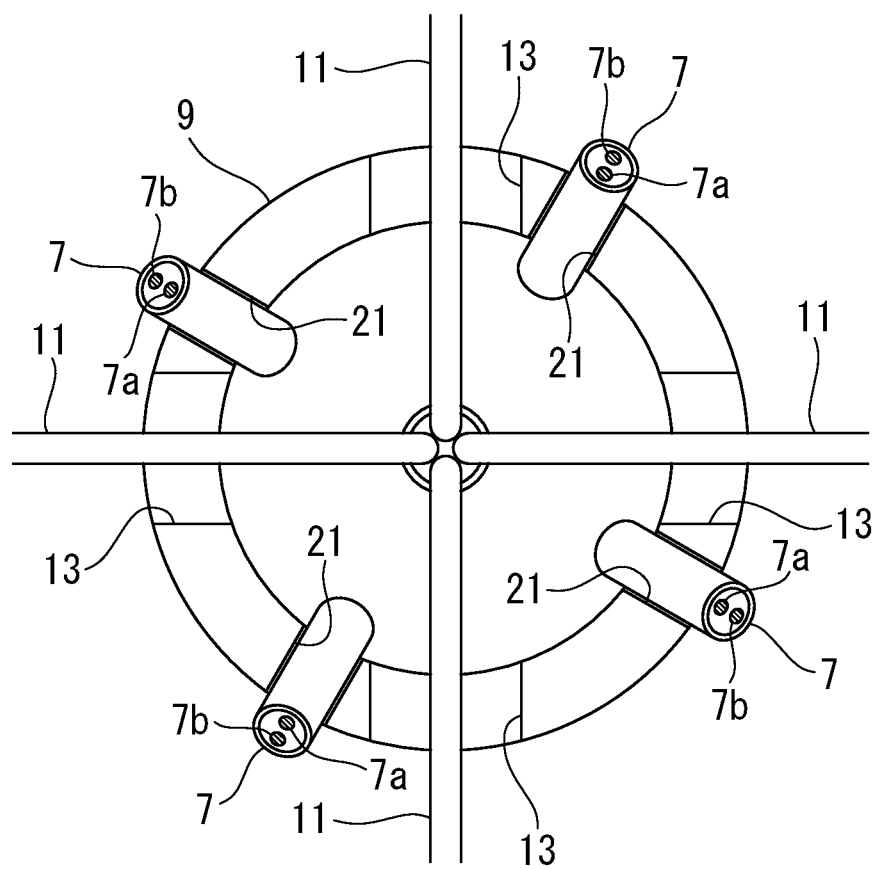
FIG. 11 is a view of a distal-end tip viewed from the distal end, showing a sixth modification of the calculus crushing device shown in FIG. 1.
Figure 12:
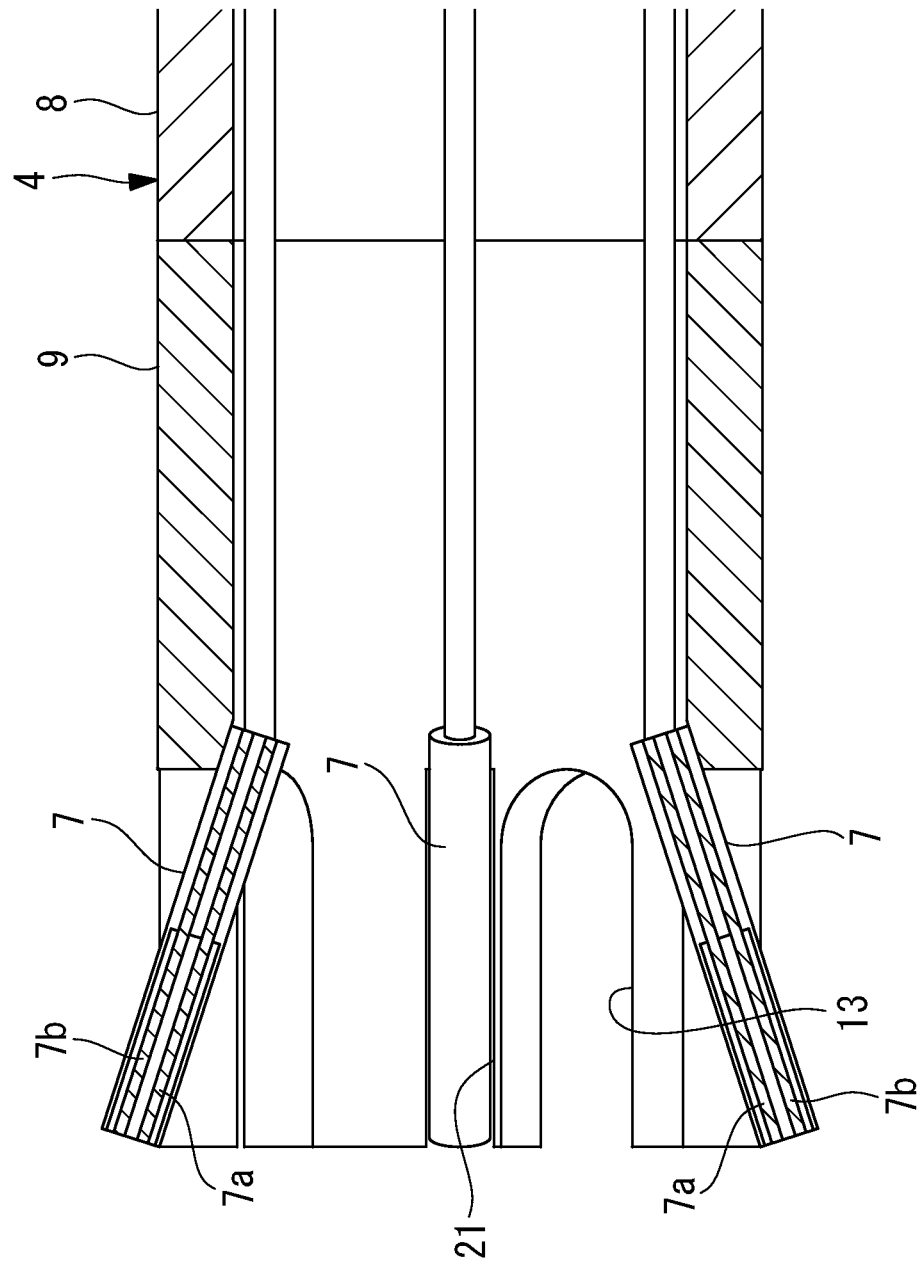
FIG. 12 is a partial longitudinal sectional view of a distal-end section of a calculus crushing device shown in FIG. 11.

Furthermore, as shown in FIGS. 11 and 12, it is also possible to provide slits 21 so as to be parallel to the escape grooves 13 of the distal-end tip 9 and to dispose the bipolar electrodes 7 through the slits 21. In this state, it is preferred that the bipolar electrodes 7 be disposed in orientations tilted outward from the inside of the distal-end tip 9 toward the distal end. According to this, there is an advantage in that it is possible to route the cable 14 inside the sheath 4 and to dispose the regions where shocks are applied to the calculus X at outer sides, thus making it easy to crush the calculus X through tying up.

Figure 13:
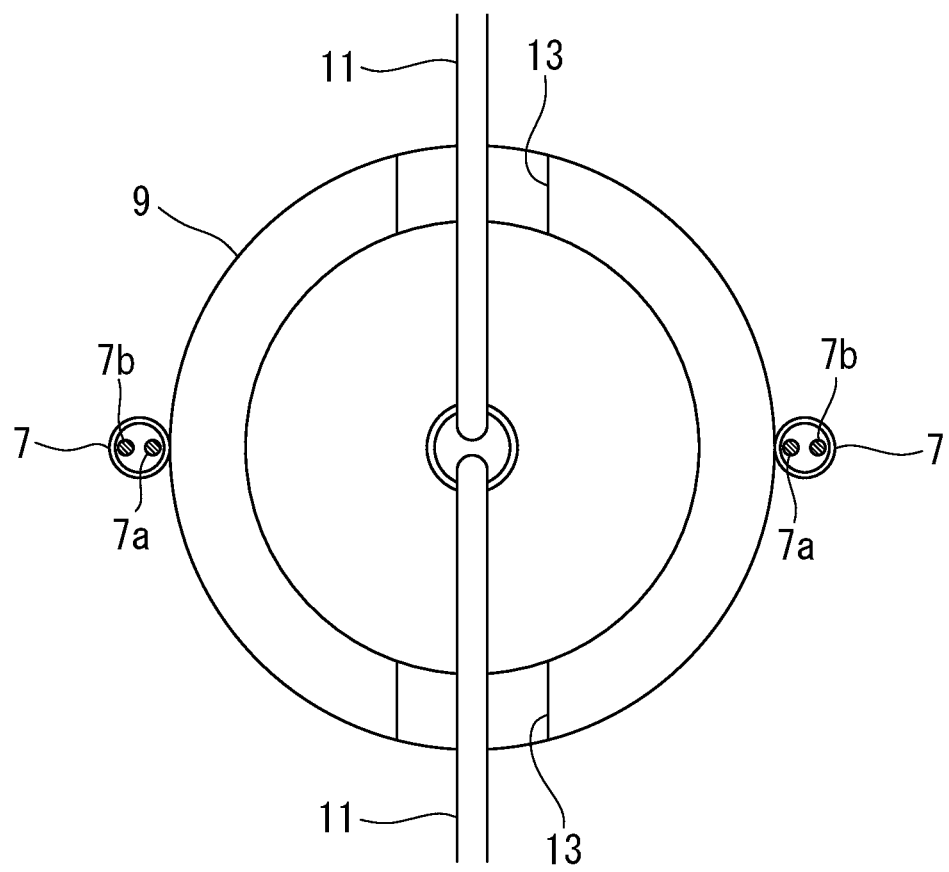
FIG. 13 is a view of a distal-end tip viewed from the distal end, showing a seventh modification of the calculus crushing device shown in FIG. 1.

Furthermore, in this embodiment, although the basket wire 6, which is formed by bundling the four wires 11, has been illustrated as a grasping part, the grasping part is not limited thereto, and the number of wires 11 is arbitrary. For example, as shown in FIG. 13, it is also possible to adopt a grasping part that is constituted of two wires 11. Accordingly, even when the number of wires 11 that constitute the grasping part is reduced, because a plurality of electrodes of the bipolar electrodes 7 are disposed at positions circumferentially different from the directions in which the wires 11 extend, it is possible to crush the calculus X from multiple directions different from the directions in which forces are applied by the wires 11.

Figure 14:
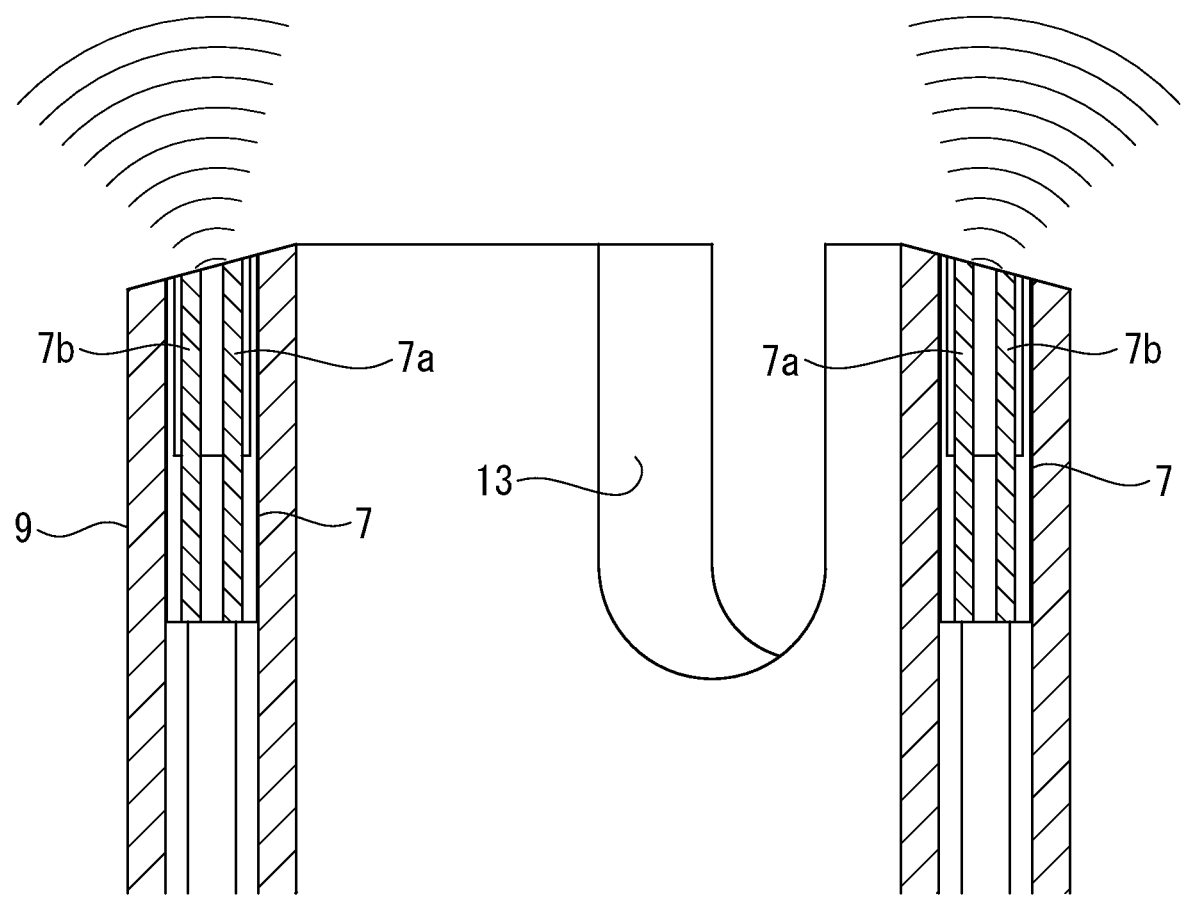
FIG. 14 is a partial longitudinal sectional view of a distal-end section, showing an eighth modification of the calculus crushing device shown in FIG. 1.
Figure 15:
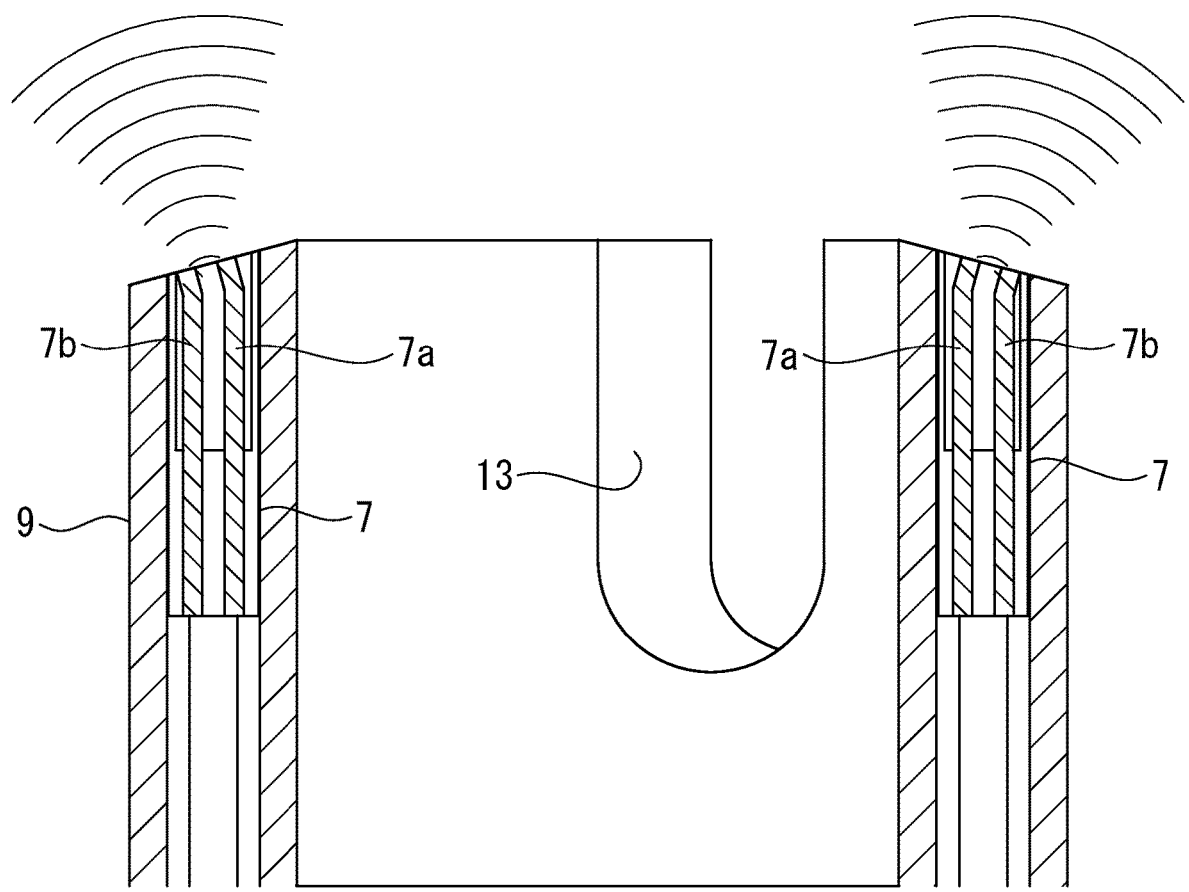
FIG. 15 is a partial longitudinal sectional view of a distal-end section, showing a ninth modification of the calculus crushing device shown in FIG. 1.

Furthermore, as shown in FIG. 14, it is also possible to incline outward only the distal-end faces of the bipolar electrodes 7, thus disposing the regions where shocks are applied to the calculus X at outer sides. Furthermore, as shown in FIG. 15, it is also possible to bend the distal ends of the positive electrodes 7a and the negative electrodes 7b of the bipolar electrodes 7 in directions in which the distal-end faces of the bipolar electrodes 7 are inclined, i.e., in directions away from the central axis of the sheath 4. Accordingly, it is possible to make the shock waves act at positions closer to the contact sites between the basket wire 6 and the calculus X.

As a result, the above-described embodiment leads to the following aspect.

One aspect of the present invention is directed to a calculus crushing device including: a tubular sheath that has a central axis; an operating wire that is disposed inside the sheath so as to be movable along the central axis; a grasping part that is provided at a distal end of the operating wire and that has one or more wires; and a bipolar electrode that is disposed at a distal end of the sheath and that applies a shock to a calculus grasped by the grasping part, wherein the sheath has, at intervals in the circumferential direction, a plurality of escape grooves that extend from the distal end of the sheath toward a proximal end of the sheath, that penetrate from an inner circumferential surface of the sheath to an outer circumferential surface thereof, and that have such dimensions as to allow the wires of the grasping part to pass therethrough; the bipolar electrode is disposed at a position shifted radially outward from the central axis and at a position between two of the escape grooves in the circumferential direction; and a distal end of the bipolar electrode is positioned closer to distal ends of the escape grooves than to proximal ends of the escape grooves.

According to this aspect, a distal-end section of the sheath is disposed inside the body, the operating wire is operated at the proximal end of the sheath, which is disposed outside the body, and the operating wire is pulled toward the proximal end in a state in which a calculus is grasped by the wires that constitute the grasping part, which is provided at the distal end of the operating wire, thus pushing the calculus against the distal end of the sheath. Because the wires that constitute the grasping part enter the escape grooves, which are provided at the distal end of the sheath, the wires pass through the escape grooves in such an inclined manner as to expand from the inside of the sheath, toward the distal end, without being caught between the grasped calculus and the sheath.

In this state, when the bipolar electrode, which is provided at the distal end of the sheath, generates a spark, electric water-pressure shock waves caused by the spark propagate to the calculus, thus making it possible to apply a shock to the calculus. Accordingly, because it becomes easy to crush the calculus, even when the tensile force to be applied to the wires that constitute the grasping part is reduced, the calculus can be crushed. Therefore, it is possible to reduce plastic deformation caused when the wires that constitute the grasping part are handled by a strong force inside the escape grooves and to easily crush a plurality of calculi.

In the above-described aspect, the bipolar electrode may include a plurality of electrodes, and the electrodes may be disposed at such positions as to sandwich at least one of the escape grooves in the circumferential direction.

With this configuration, the electric water-pressure shock waves are made to propagate to the calculus from both sides that sandwich each of the wires, which pass through the escape grooves, in the circumferential direction, thus making it possible to generate cracks in the vicinities of positions at which the calculus is tightened by the wires that constitute the grasping part. Accordingly, crushing of the calculus performed by the grasping part can be further facilitated.

Furthermore, in the above-described aspect, each of the electrodes may be disposed at a position closer to one of two of the escape grooves than to a center position of the two of the escape grooves, in the circumferential direction.

With this configuration, for the wires that pass through the escape grooves, the electric water-pressure shock waves are made to propagate to the calculus from the positions each closer to one of two of the escape grooves than to the center position of the two of the escape grooves in the circumferential direction, thus making it possible to generate cracks in the vicinities of positions at which the calculus is tightened by the wires that constitute the grasping part. Accordingly, crushing of the calculus performed by the wires that constitute the grasping part can be further facilitated.

Furthermore, in the above-described aspect, the bipolar electrode may be disposed in an orientation tilted radially outward, toward the distal end.

With this configuration, regions where the electric water-pressure shock waves are made to propagate to the calculus can be located away from the center of the calculus, thus making it possible to generate cracks in the vicinities of positions at which the calculus is tightened by the wires that constitute the grasping part.

Furthermore, the above-described aspect may further include, between the escape grooves, an electrode placement section that extends from proximal ends of the escape grooves toward distal ends thereof, wherein the bipolar electrode may be fixed to the electrode placement section.

According to the present invention, an advantageous effect is afforded in that plastic deformation of wire strands is prevented, thus making it possible to facilitate crushing of a plurality of calculi.

REFERENCE SIGNS LIST 1 calculus crushing device
4 sheath
5 operating wire
6 basket wire (grasping part)
7 bipolar electrode
7a positive electrode (electrode)
7b negative electrode (electrode)
11 wire
13 escape groove
X calculus

The invention claimed is:

1. A treatment device comprising:
 a tubular sheath having a central axis;
 an operating wire disposed inside the sheath so as to be movable along the central axis;
 a grasping part provided at a distal end of the operating wire, the grasping part having a plurality of wires; and
 at least one bipolar electrode disposed at a distal end of the sheath, the at least one bipolar electrode is configured to apply a shock to a processing target grasped by the grasping part,
 wherein the sheath has, at intervals in a circumferential direction, a plurality of escape grooves, each of the plurlaity of escape grooves being configured to:
  extend from a distal end surface of the sheath toward a proximal end of the sheath, and
  penetrate from an inner circumferential surface of the sheath to an outer circumferential surface of the sheath,
 each of the plurlaity of escape grooves is dimensioned to allow a respective wire of the plurality of wires to pass therethrough;
 the at least one bipolar electrode is disposed at a position shifted radially outward from the central axis and at a position between two escape grooves of the plurality of escape grooves in the circumferential direction; and
 a distal end of the at least one bipolar electrode is positioned closer to distal ends of the two escape grooves than to proximal ends of the two escape grooves.

2. The treatment device according to claim 1, wherein the at least one bipolar electrode is disposed in an orientation tilted radially outward relative to the central axis.

3. The treatment device according to claim 1, further comprising an electrode placement section that extends, between the two escape grooves, from the proximal ends of the two escape grooves toward the distal ends of the two escape grooves,
 wherein the at least one bipolar electrode is fixed to the electrode placement section.

4. The treatment according to claim 1, wherein the at least one bipolar electrode comprises a plurality of bipolar electrodes, and each bipolar electrode of the plurality of bipolar electrodes is disposed between two adjacent wires of the plurality of wires in the circumferential direction.

5. The treatment according to claim 1, wherein the at least one bipolar electrode is disposed at a center of the two escape grooves in the circumferential direction.

6. The treatment according to claim 1, wherein the at least one bipolar electrode is disposed at a position closer to one of the two escape grooves than to a center of the two escape grooves in the circumferential direction.

7. The treatment device according to claim 1, wherein the distal end of the at least one bipolar electrode is configured to be disposed at a position close to a surface of the processing target in a state in which the processing target abuts against the distal end of the sheath.

8. The treatment device according to claim 1, wherein a distal end surface of the at least one bipolar electrode is offset proximally from the distal end surface of the sheath.

9. The treatment device according to claim 1, wherein
the at least one bolpolar electrode comprises a plurlaity of bipolar electrodes each disposed at a position shifted radially outward from the central axis and at a position between two escape grooves of the plurality of escape grooves in the circumferential direction; and
a distal end of each bipolar electrode of the plurlaity of bipolar electrodes is positioned closer to distal ends of the two escape grooves than to proximal ends of the two escape grooves.

10. A treatment device comprising:
a tubular sheath having a central axis;
an operating wire disposed inside the sheath so as to be movable along the central axis;
a grasping part provided at a distal end of the operating wire, the grasping part having a plurality of wires; and
a plurality of bipolar electrodes disposed at a distal end of the sheath the plurality of bipolar electrodes are each configured to apply a shock to a calculus grasped by the grasping part,
wherein the sheath has, at intervals in a circumferential direction, a plurality of escape grooves, each of the plurlaity of escape grooves being configured to:
extend from a distal end surface of the sheath toward a proximal end of the sheath, and
penetrate from an inner circumferential surface of the sheath to an outer circumferential surface of the sheath,
each of the plurlaity of escape grooves is dimensioned to allow a respective wire of the plurality of wires to pass therethrough;
the plurality of bipolar electrodes are each disposed at a position shifted radially outward from the central axis and at a position between two escape grooves of the plurality of escape grooves in the circumferential direction and are disposed at positions so as to sandwich at least one of the plurlaity of escape grooves in the circumferential direction; and
distal ends of the plurlaity of bipolar electrodes are positioned closer to distal ends of the plurlaity of escape grooves than to proximal ends of the plurlaity of escape grooves.

11. The treatment device according to claim 10, wherein each of the plurlaity of bipolar electrodes are disposed at a position closer to one of two escape grooves than to a center of the two escape grooves in the circumferential direction.

12. A treatment device comprising:
a sheath having a longitudinal axis;
an operating wire located in the sheath and configured to move along the longitudinal axis;
a grasping part located at a distal end of the operating wire, the grasping part having a plurality of wires; and
at least one electrode located at a distal end of the sheath,
wherein the sheath has, in a circumferential direction, a plurality of grooves that extend from a distal end surface of the sheath toward a proximal end of the sheath,
the plurality of the grooves penetrate from an inner circumferential surface of the sheath to an outer circumferential surface of the sheath, and
each of the plurality of the grooves being dimensioned to allow a respective wire of the plurality of wires to pass therethrough.

13. The treatment device according to claim 12, wherein the at least one electrode is located at a position shifted radially outward from the longitudinal axis and at a position between two of the plurality of the grooves in the circumferential direction.

14. The treatment device according to claim 12, wherein a distal end surface of the at least one electrode is offset proximally from the distal end surface of the sheath.

15. The treatment device according to claim 14, wherein a distal end of the at least one electrode is located closer to distal ends of the plurality of grooves than to proximal ends of the plurality of grooves.

16. The treatment device according to claim 12, wherein a distal end of the at least one electrode is configured to be located at a position close to a surface of a processing target grasped by the grasping part in a state in which the processing target abuts against the distal end of the sheath.

17. The treatment device according to claim 12, wherein a distal end of the at least one electrode is located distally relative to proximal ends of the plurality of the grooves.

18. The treatment device according to claim 12, wherein the at least one electrode comprises a plurality of electrodes, each electrode of the plurality of electrodes is disposed between two adjacent wires of the plurality of wires in the circumferential direction.

19. The treatment device according to claim 12, wherein the at least one electrode is located on the inner circumferential surface of the sheath.

20. The treatment device according to claim 12, wherein the at least one electrode is located on the outer circumferential surface of the sheath.

* * * * *